US012790412B2

(12) United States Patent
Rodriguez et al.

(10) Patent No.: US 12,790,412 B2
(45) Date of Patent: Nov. 10, 2026

(54) METHOD FOR OBTAINING LOW MOLECULAR WEIGHT HEPARINS AND LOW MOLECULAR WEIGHT HEPARINS OBTAINED THEREFROM

(71) Applicant: LABORATORIOS FARMACEUTICOS ROVI, S.A., Madrid (ES)

(72) Inventors: Guillermo Franco Rodriguez, Madrid (ES); Ibon Gutierro Aduriz, Madrid (ES)

(73) Assignee: LABORATORIOS FARMACEUTICOS ROVI, S.A., Madrid (ES)

( * ) Notice: Subject to any disclaimer, the term of this patent is extended or adjusted under 35 U.S.C. 154(b) by 773 days.

(21) Appl. No.: 18/050,242

(22) Filed: Oct. 27, 2022

(65) Prior Publication Data

US 2023/0139786 A1 May 4, 2023

Related U.S. Application Data

(63) Continuation-in-part of application No. PCT/ES2020/070695, filed on Nov. 10, 2020, which is a continuation-in-part of application No. PCT/ES2020/070271, filed on Apr. 27, 2020.

(51) Int. Cl.
*C08B 37/00* (2006.01)
*A61K 31/727* (2006.01)

(52) U.S. Cl.
CPC ........ *C08B 37/0075* (2013.01); *A61K 31/727* (2013.01)

(58) Field of Classification Search
CPC .......................... C08B 37/0075; A61K 31/727
See application file for complete search history.

(56) References Cited

U.S. PATENT DOCUMENTS

| | | | |
|---|---|---|---|
| 3,179,566 | A | 4/1965 | Horner et al. |
| 4,281,108 | A | 7/1981 | Fussi |
| 4,929,699 | A | 5/1990 | Wilson et al. |
| 4,973,580 | A | 11/1990 | Mascellani et al. |
| 6,384,021 | B1 | 5/2002 | Mardiguian |
| 7,968,082 | B1 | 6/2011 | Shriver |
| 8,802,156 | B2 | 8/2014 | Franco Rodriguez |
| 8,822,659 | B2 | 9/2014 | Lopez-Belmonte Encina |
| 9,211,305 | B2 | 12/2015 | Encina |
| 10,705,037 | B2 | 7/2020 | Franco Rodriguez |
| 10,809,212 | B2 | 10/2020 | Franco Rodriguez |
| 2011/0201572 | A1 | 8/2011 | Lopez-Belmonte Encina |
| 2011/0306757 | A1 | 12/2011 | Lopez-Belmonte Encina |
| 2014/0066402 | A1 | 3/2014 | Lopez-Belmonte Encina |

FOREIGN PATENT DOCUMENTS

| | | | | |
|---|---|---|---|---|
| CN | 102399379 A * | 4/2012 | | |
| EP | 0101141 A3 | 2/1984 | | |
| EP | 0040144 B | 8/1984 | | |
| EP | 2213282 A1 | 4/2010 | | |
| EP | 2881404 B1 | 3/2018 | | |
| ES | 2336297 B1 | 1/2011 | | |
| ES | 2340902 B1 | 4/2011 | | |
| WO | 2010000904 A1 | 1/2010 | | |
| WO | 2010040880 A1 | 4/2010 | | |
| WO | 2010086425 A1 | 8/2010 | | |
| WO | WO-2014020227 A1 * | 2/2014 | ......... | C08B 37/0078 |

OTHER PUBLICATIONS

Nurunnabi, Md et al., Quant Imaging Med Surg, "Heparin based nanoparticles for cancer targeting and noninvasive imaging", 2012, vol. 2, No. 3, pp. 219-226 (Year: 2012).*

Shen, Xuemin et al., International Journal of Biological Macromolecules, "Development of low molecular weight heparin by H2O2/ ascorbic acid with ultrasonic power and its anti-metastasis property", Apr. 2019, vol. 133, pp. 101-109 (Year: 2019).*

Guan, Y. et al., Journal of Pharmaceutical Sciences, "Comparison of Low-Molecular-Weight Heparins Prepared from Bovine Lung Heparin and Porcine Intestine Heparin", 2016, vol. 105, pp. 1843-1850 (Year: 2016).*

Jeske, W. et al., Blood, "Effect of 1,6-Anhydro Bicyclic Ring Structure on the Pharmacokinetic and Pharmacodynamic Behavior of Low Molecular Weight Heparin", 2004, vol. 11, 1868 (Year: 2004).*

Oliveira et al. (Structural and functional analyses of biosimilar enoxaparina available in Brazil in Thromb. Heamo. (2014), 113(1), 53-65.

Linhardt et al. ("Mapping and quantification of the major oligosaccharides component of heparin", in Biochem. J. (1988), 254, 781-787).

Tran et al. ("Anticoagulant therapy for major arterial and venous thromboembolism", in Basic principles and clinical practice (Colman RW, Marder VJ, Clowes AW, George JN, Goldhaber SZ (Ed). Lippincott Williams and Wilkins; 2006:1673-1688).

Xu et al. ("Chemoenzymatic synthesis of homogenous ultra low molecular weight heparins", in Science (2011), 334, 498-501).

Langeslay et al. ("Advancing Analytical Methods for Characterization of Anionic Carbohydrate Biopolymers", Langeslay D.J. PhD Thesis UC Riverside 2013).

Beni et al. ("Analysis and characterization of heparin impurities", in Anal. Bioanal. Chem. (2011), 399, 527-539).

(Continued)

*Primary Examiner* — Bahar Craigo

(74) *Attorney, Agent, or Firm* — Innovar, L.L.C.; Rick Matos

(57) ABSTRACT

The invention relates to a method for obtaining low molecular weight heparins which exhibit high stability. The method includes the treatment of depolymerized heparin with $H_2O_2$ in a ratio of between 0.04 and 1.0 liters of $H_2O_2$ (30-35% w/v in water) per kg of depolymerized heparin. The invention also relates to a low molecular weight heparin obtained by this method, pharmaceutical compositions of the same, and methods of treatment employing the same.

23 Claims, 2 Drawing Sheets

(56) References Cited

OTHER PUBLICATIONS

Casu et al. ("Characterization of Sulfation Patterns of Beef and Pig Mucosal Heparins by Nuclear Magnetic Resonance", in Arzneim.-Forsch./Drug Res. (1996), 46, 472-477).
Keire et al. ("Characterization of currently marketed heparin products: composition analysis by 2D-NMR", in Anal. Methods (2013), 5, 2984-2994).
Ozug et al. ("Structural elucidation of the tetrasaccharide pool in enoxaparin sodium", in Anal. Bioanal. Chem. (2002), 403, 2733-2744).
Bisio et al. ("Structural features of low molecular weight heparins affecting their affinity to antithrombin", in Thromb. Hemost. (2009), 102, 865-873).
Guerrini et al. ("Low-molecular-weight heparins: structural differentiation by two-dimensional nuclear magnetic resonance spectroscopy", in Semin. Thromb. Hemost. (2007), 33, 478-487).
Malz et al. ("Validation of quantitative NMR", in Journal of Pharmaceutical and Biomedical Analysis (2005), 38, 813-823).
Glauser et al. ("Generic versions of enoxaparin available for clinical use in Brazil are similar to the original drug", in J. Thromb. Haemost. (2011), 9, 1419-1422).
Desai et al. ("Molecular Weight of Heparin using 13C Nuclear Magnetic Resonance Spectroscopy", in J. Pharm. Sci. (1995), 84(2), 212-215).
Mourier et al. ("Analytical and Statistical Comparability of Generic Enoxaparina from the US Market with the Originator Product", in J. Pharm. Biomed. Anal. (2015), 115(29), 431-442).
Franchini et al. ("The evolution of anticoagulant therapy", in Blood Trans. (2016), 14(2), 175-184).
Lima et al. ("Ultra-low-molecular-weight heparins: precise structural features impacting specific anticoagulant activities", in Thromb. Haemo. (2013), 109(3), 471-478).

* cited by examiner

METHOD FOR OBTAINING LOW MOLECULAR WEIGHT HEPARINS AND LOW MOLECULAR WEIGHT HEPARINS OBTAINED THEREFROM

CROSS-REFERENCE TO RELATED APPLICATIONS

The present application is continuation-in-part of PCT/ES2020/070695 filed Nov. 10, 2020, which is a continuation-in-part of PCT/ES2020/070271 filed Apr. 27, 2020, the entire disclosures of which are hereby incorporated by reference.

FIELD OF THE INVENTION

The present invention relates to a process for the preparation of low molecular weight heparins (LMWH) and to the low molecular weight heparins obtained by that process. The LMWHs of the invention are also useful for methods of treatment and for inclusion in pharmaceutical compositions.

BACKGROUND OF THE INVENTION

Heparin is a polysaccharide of the glycosaminoglycan family, formed by uronic acid (L-iduronic acid or D-glucuronic acid) and D-glucosamine, alternately bound. The L-iduronic acid may be 2-O-sulfated and the D-glucosamine may be N-sulfated and/or 6-O-sulfated, and to a lesser extent N-acetylated or 3-O-sulfated. The heparin is preferably used as a sodium salt but can also be used as a salt of other alkali or alkaline earth metals and is mainly used as an antithrombotic and anticoagulant drug.

It is known in the industry that LMWH products prepared by distinctly different processes are dissimilar in physical, chemical, and biological properties. Accordingly, changes in the depolymerization process could result in substantial variation of the structure or composition of a given LMWH. It is recommended that for every LMWH a defined depolymerization procedure is needed to guarantee the sameness of the final LMWH product and the predictability of clinical outcomes. The United States Food and Drug Administration, the European Medicines Agency, and the World Health Organization, regard LMWHs as individual products that should not be considered as clinically equivalent, as they differ in many aspects such as molecular, structural, physiochemical, and biological properties.

U.S. Pat. No. 3,179,566 A to Horner et al. discloses the treatment of heparin with hydrogen peroxide to decolorize the heparin. LMWH is not formed. U.S. Pat. No. 4,281,108A discloses a process for depolymerizing heparin in an autoclave with hydrogen peroxide by heating at a pressure preferably between 1 and 2 atm to form heparins, with different mean molecular weights (MW) in a range approximately between 12,000 and 4,000 D, starting from normal heparin of MW=15,000 D. U.S. Pat. No. 4,533,549A discloses a process for depolymerizing heparin by using a combination of ascorbic acid and hydrogen peroxide at 22C. EP0121067B discloses a process for depolymerizing heparin by using a combination of ascorbic acid, cupric acetate, and hydrogen peroxide.

Heparins can be classified according to their molecular weight into unfractionated heparin (UFH), LMWH and very low molecular weight heparin (VLMWH). LMWH and VLMWH are obtained by depolymerization of the original UFH molecule.

Several methods for the preparation of LMWH have been described in the prior art. One of them corresponds to alkaline depolymerization by a β-elimination mechanism.

EP0040144 describes a process for obtaining LMWH by a method comprising the steps of transalkylation of a heparin salt into benzethonium heparinate, esterification of the benzethonium heparinate with benzyl chloride, purification to obtain the sodium salt of the benzyl ester of the heparin, depolymerization with sodium hydroxide with saponification of the ester and purification of the product.

EP1070503 describes a process for obtaining LMWH by a method comprising the steps of transalkylation of a heparin salt in benzalkonium heparinate, depolymerization in non-aqueous medium with Triton B, and purification of the product.

EP2881404 describes a process for obtaining LMWH comprising a first transalkylation step, depolymerization with a phosphazene base or a guanidine-derived base and a final transalkylation.

EP101141A2 to Smith et al. discloses a method of forming LMWH by treating heparin with acid to form heparinic acid and then depolymerizing the heparinic acid with heat in the presence of an oxidizing agent.

HU203565B discloses a process for depolymerizing heparin with hydrogen peroxide to form LMWH having a molecular weight of 1700-8000 Da. The depolymerization is conducted preferably in an aqueous solution of 5-20%, more preferably 5-15%, at 30-70° C., with peroxide or peracid such as hydrogen peroxide in the presence of a 0.001-0.1 molar catalytic amount of a metal such as $Cu^{++}$ or $Fe^{++}$.

Prior art methods, however, produce LMWH that exhibit reduced stability and exhibit a 1,6-anhydro residue content at the reducing terminus of its oligosaccharide chains, which is disadvantageous, especially towards stability of the resulting LMWH.

There is a need for a process of preparing LMWHs that exhibit improved stability while maintaining acceptable anti-FXa and anti-FIIa activity for a greater period.

SUMMARY OF THE INVENTION

The present invention seeks to overcome the disadvantage(s) of prior art processes for preparing LMWHs and to provide LMWH exhibiting improved characteristics.

The inventors of the present invention have developed an improved method of preparing low molecular weight heparins (LMWH) which exhibit superior stability, while maintaining good anti-FXa and anti-FIIa activity. This method of preparation of LMWH comprises treating crude depolymerized heparin with $H_2O_2$ in a ratio of between 0.04 and 1.0 liters of $H_2O_2$ (about 30-36% w/v or about 32-34% w/v, or about 33% w/v in water) per kg of depolymerized heparin, or salt thereof, thereby forming the LMWH.

An aspect of the invention provides a method of preparing LMWH comprising the step of treating depolymerized heparin with about 0.04-1 L of $H_2O_2$ (about 30-35% wt/v in water) per Kg of depolymerized heparin, wherein said treating is conducted at a temperature of about 20-40° C. for a period of about 3 h or more, about 8 h or more, about 12 h or more, or of about 3-48 h, about 3-7 h, about 4-6 h, about 8-48 h, about 12-48 h, or about 24-48 h.

In some aspects, the invention provides a method of preparing LMWH as defined herein, the method comprising the steps of a) providing heparin salt; b) depolymerizing said salt to form depolymerized heparin; and c) treating said depolymerized heparin one or more times with aqueous hydrogen peroxide solution to form said LMWH. In some embodiments, the depolymerizing step is conducted with a quaternary ammonium hydroxide. In some embodiments, the treating step is conducted with about 0.04-1 L of $H_2O_2$ (about 30-35% wt/v in water) per Kg of depolymerized heparin. In some embodiments, the heparin salt is a benzalkonium heparin salt.

The invention also provides a method of preparing LMWH as defined herein, the method comprising the steps of a) providing benzalkonium heparin salt; b) depolymerizing said salt with quaternary ammonium hydroxide to form depolymerized heparin; and c) treating said depolymerized heparin one or more times with about 0.04-1 L of $H_2O_2$ (about 30-35% wt/v in water) per Kg of depolymerized heparin, thereby forming said LMWH. The method can further comprise the step of precipitating said LMWH one or more times with a solution of sodium acetate in methanol, thereby forming LMWH sodium salt.

Embodiments of the invention include those wherein a) the molecular weight of the LMWH is in the range of about 3-3.8 KDa or about 3-3.6 KDa; b) the LWMH exhibits a 1,6-anhydro residue content of less than about 15%, less than about 13%, less than about 11%, or of about 1-15%, about 2-13% or about 4-11% at the reducing terminus of its oligosaccharide chains; c) the LMWH exhibits a molar ratio of 1,6-anhydroglucosamine residues: 1,6-anhydromannosamine residues that is greater than or equal to about 1:1, or in the range of about 1:1 to about 3:1, about 1:1 to about 2.5:1, or about 1.05:1 to about 2.5:1; d) the LMWH exhibits an anti-FXa activity of at least about 80 IU/mg or in the range of about 80-120 IU/mg or about 95-120 IU/mg; e) the LMWH exhibits an anti-FIIa activity of at least about 5 IU/mg or in the range of about 5-20 IU/mg, or about 10-20 IU/mg; f) the LMWH exhibits a degree of coloration greater than or equal to 6 in the range of color reference solutions established in European Pharmacopoeia chapter 2.2.2. (method II) for at least 24 months or at least 36 months after storage at room temperature (about 20-22° C., or about 21° C.) at 60% relative humidity; g) the LMWH is included in a lyophilized composition; h) the starting heparin is of the grade defined in the European Pharmacopoeia or the US Pharmacopoeia; h) the starting heparin has been obtained from pig intestinal mucosa; i) the LMWH is present as a sodium salt; j) the content of 1,6-anhydroglucosamine residues in the LMWH is less than about 1.1% mol., less than about 1% mol., or in the range of about 0.1-1.1% mol., or of about 0.1-1% mol; k) the content of 1,6-anhydromannosamine residues in the LMWH is less than about 1.2% mol., less than about 1.1% mol., less than about 1% mol, or in the range of about 0.05-1.2% mol., about 0.05-1.1% mol., or about 0.05-1% mol.; and/or l) the content (proportion) of 1,6-anhydroglucosamine residues is equal to or greater than the content of 1,6-anhydromannosamine residues in the LMWH.

Embodiments of the invention also include those wherein the process further comprises one or more of the following steps: a) depolymerizing heparin to form depolymerized heparin; b) preparing an aqueous solution of heparin sodium, adding benzalkonium chloride to said solution to form benzalkonium heparinate, dissolving said benzalkonium heparinate in $CH_2Cl_2$, adding Triton B to the dissolved benzalkonium heparinate, thereby forming depolymerized heparin; c) after completion of the treating step(s), adding a solution of sodium acetate in methanol, thereby precipitating the crude LMWH; d) lyophilizing a solution comprising the LMWH, thereby forming lyophilized LMWH; e) precipitating the depolymerized heparin between sequential steps of treating the depolymerized heparin with $H_2O_2$; f) precipitating the depolymerized heparin in aqueous solution with a solution of sodium acetate in methanol between sequential steps of treating the depolymerized heparin with $H_2O_2$; g) after the first treatment with $H_2O_2$, precipitating the depolymerized heparin in aqueous solution with a solution of sodium acetate in methanol; h) purifying the LMWH by way of a precipitation with a solution of sodium acetate in methanol; i) washing the benzalkonium heparinate with aqueous solution (water) prior to mixing it with Triton B; j) drying the benzalkonium heparinate prior to mixing it with $CH_2Cl_2$ and/or Triton B; k) forming a heparin salt and depolymerizing said salt to form depolymerized heparin; and/or l) isolating said LMWH as a LMWH salt. Independently upon each occurrence, sodium acetate is included with the methanol during a precipitating step.

Embodiments of the invention also include those wherein a) the mixture of benzalkonium heparinate, $CH_2Cl_2$, and Triton B is maintained at a temperature of about 20-40° C. for a period of at least about 8 h, at least about 24 h, or about 24-48 h, thereby forming depolymerized heparin; b) the treating step is conducted in two or more treating substeps by adding respective two or more portions of the $H_2O_2$ solution to the depolymerized heparin and allowing the respective portions to react with the depolymerized heparin for respective periods; c) the treating step is conducted by sequentially treating the depolymerized benzalkonium heparinate with two or more portions of $H_2O_2$ solution, wherein each portion is allowed to react for at least about 3 h at a temperature of at least about 20° C. before addition of a subsequent portion; d) the treating step is conducted at pH in the range of about 10.5-11.5; e) the weight ratio of Triton B:benzalkonium heparinate is about 0.2:1 to 0.3:1 or about 0.25:1; f) the Triton B is present at 40% w/v in methanol when being added to the benzalkonium heparinate; g) the benzalkonium heparinate is prepared by treating sodium heparinate in water with a solution of benzalkonium chloride (50% w/v) in water at a temperature in the range of about 25-35° C.; and/or h) the quaternary ammonium hydroxide is selected from the group consisting of benzyltrimethylammonium hydroxide (Triton B) and benztriethylammonium hydroxide.

Embodiments of the invention include those wherein the treatment with hydrogen peroxide is conducted in the absence of metal salt, e.g. in the absence of $Cu^{++}$ salt, $Fe^{++}$ salt, or ascorbic acid. The invention also includes embodiments wherein the treatment with hydrogen peroxide is not conducted in an autoclave and/or is conducted at atmospheric pressure.

A first aspect of the invention relates to a method for obtaining low molecular weight heparins with an average molecular weight of between 3 and 3.8 KDa, comprising the following steps:

a) preparing an aqueous solution of heparin sodium;
b) adding benzalkonium chloride to the solution of step a) to obtain benzalkonium heparinate;
c) dissolving the benzalkonium heparinate obtained in step b) in $Cl_2CH_2$, adding Triton B to that solution, and maintaining a temperature between 2° and 40° C. for 24 to 48 hours; and
d) carrying out at least two treatments with $H_2O_2$ of the depolymerized heparin obtained in step c) in a ratio of between 0.04 and 1.0 liters of $H_2O_2$ at 33% w/v for each kg of depolymerized heparin in each treatment.

A second aspect of the invention relates to a low molecular weight heparin obtainable by the method of the invention.

It has been found that the obtained LMWHs exhibit a 1,6-anhydro residue content of between 1 and 15%, in the range of about 1-15%, or less than about 15%. Therefore, a third aspect of the invention relates to a low molecular weight heparin with an average molecular weight of between 3 and 3.8 kDa having a 1,6-anhydro residue content of between 1 and 15% at the reducing terminus of its oligosaccharide chains.

The LMWHs of the invention have an average molecular weight (Mw) of in the range of about 3-3.8 kDa, preferably in the range of about 3-3.6 kDa.

In one embodiment, the LMWH of the invention has a 1,6-anhydro residue content in the range of about 1-15% (or less than about 15%) at the reducing terminus of its oligosaccharide chains; preferably in the range of about 2-13%, more preferably in the range of about 4-11%. The present inventors have discovered that a LMWH with this particular 1,6-anhydro terminus residue content at the terminal ends exhibits substantially improved stability. On the other hand, LMWHs made by prior art processes have a 1,6-anhydro terminus residue content above 15% and those LMWHs exhibit substantially reduced stability.

Preferably, the molar content of the 1,6-anhydroglucosamine residues in the LMWH of the invention is greater than or equal to that of the 1,6-anhydromannosamine residues. In a particular embodiment, the molar ratio of 1,6-anhydroglucosamine residues: 1,6-anhydromannosamine residues in the LMWH is in the range of about 1:1 to about 3:1, preferably from about 1:1 to about 2.5:1 or from about 1.05:1 to about 2.5:1.

In a particular embodiment of the invention, the LMWH has an average molecular weight as determined by size exclusion chromatography (as defined in European Monograph 0828) in the range of about 3 to about 3.8 kDa, a 1,6-anhydro residue content of about 1-15% (or less than about 15%) at the reducing terminus of their oligosaccharide chains, and a molar ratio of 1,6-anhydroglucosamine residues to 1,6-anhydromannosamine residues that is greater than or equal to about 1:1, preferably in the range of about 1:1 to about 3:1.

Preferably, the LMWH of the invention exhibits an anti-FXa activity of at least about 80 IU/mg or in the range of about 80-120 IU/mg and an anti-FIIa activity of at least about 5 IU/mg or in the range of about 5-20 IU/mg. In a particular embodiment, it exhibits an anti-FXa activity in the range of about 95-120 IU/mg and an anti-FIIa activity in the range of about 10-20 IU/mg.

In a particular embodiment of the invention, the LMWH has an average molecular weight of about 3 to about 3.8 kDa, a 1,6-anhydro residue content of about 1-15% (or less than about 15%) at the reducing terminus of their oligosaccharide chains, and a molar ratio of 1,6-anhydroglucosamine residues to 1,6 anhydromannosamine residues greater than or equal to about 1:1, preferably in the range of about 1:1 to about 3:1, an anti-FXa activity of about 80-120 IU/mg and an anti-FIIa activity of about 5-20 IU/mg.

Preferably, the LMWH of the invention presents a degree of coloration greater than or equal to 6 in the range of color reference solutions established in European Pharmacopoeia chapter 2.2.2. (method II), for at least 24 months, preferably for at least 36 months, at room temperature and 60% relative humidity. This determination can be done following the method described in the European Pharmacopoeia (chapter 2.2.2; method II), or automatically using a colorimeter.

It has been observed that the LMWHs of the invention exhibit high stability. In particular, it has been observed that they are stable for at least 24 months, or even for at least 36 months at room temperature and 60% relative humidity. The storage condition can be about atmospheric pressure or less than atmospheric pressure. The LMWH can be stored in colorless or colored sealed container. The container can comprise glass or plastic or other pharmaceutically acceptable container. The content of oxygen in the sealed container is preferably less than about 1 ppm, less than about 0.5 ppm, or less than about 0.3 ppm.

In one aspect, the invention relates to a method for obtaining low molecular weight heparins with an average molecular weight of about 3-3.8 KDa mass average molecular weight (as per European pharmacopoeia) or of about 3-3.8 KDa weight average molecular weight as per US pharmacopoeia, the method comprising the following steps:

a) preparing an aqueous solution of heparin sodium;
b) adding benzalkonium chloride to the solution of step a) to obtain benzalkonium heparinate;
c) dissolving the benzalkonium heparinate obtained in step b) in $CH_2CH_2$, adding Triton B and maintaining a temperature between 2° and 40° C. for 24 to 48 hours; and
d) at least twice, treating the depolymerized heparin obtained in step c) with $H_2O_2$ at a ratio of about 0.04-1.0 liters of $H_2O_2$ at 33% w/v for each kg of depolymerized heparin in each treatment.

In some embodiments, the invention provides a method of producing LMWH with an average molecular weight of about 3-3.8 KDa, the method comprising:

a) providing an aqueous solution of heparin sodium;
b) adding benzalkonium chloride to the solution of step a) to obtain benzalkonium heparinate;
c) separating the benzalkonium heparinate from the aqueous solution;
d) dissolving the benzalkonium heparinate of step c) in $CH_2CH_2$, adding at least one portion of Triton B to that mixture, and maintaining a temperature of at least about 20° C. for at least about 8 hours, thereby forming depolymerized heparin;
e) sequentially treating the depolymerized benzalkonium heparinate of step d) with two or more portions of $H_2O_2$ solution, wherein each portion is allowed to react for at least about three hours at a temperature of at least about 20° C. before addition of a subsequent portion; and
f) treating the solution of step e) with a solution of sodium acetate in methanol, thereby precipitating crude LMWH.

Embodiments of the invention include those wherein i) the concentration of heparin sodium in the solution of step a) is in the range of about 10-15% w/v; ii) the molar ratio of benzalkonium chloride to heparin sodium is in the range of about 3-6% w/v; iii) the benzalkonium chloride is present as an about 50% w/v aqueous solution that is added to the solution of step a); iv) the concentration of benzalkonium heparinate in the $CH_2Cl_2$ is in the range of about 20-30% w/v); v) the weight ratio of Triton B to benzalkonium heparinate is in the range of about 0.2:1 to 0.3:1; vi) the Triton B is present as an about 35-45% or about 40% w/v in methanol prior to addition to the benzalkonium heparinate in the $CH_2Cl_2$; vii) for step d), the temperature is maintained for at least about 24 hours; viii) the Triton B is added in at least two portions; ix) the Triton B is added in at least three portions; x) the temperature of step d) is maintained at about 25-35° C.; xi) the $H_2O_2$ solution comprises about 30-35% w/v of $H_2O_2$ in water; and/or xii) for each portion of $H_2O_2$ solution added, about 0.04-1.0 liters of the solution is added per Kg of benzalkonium heparinate.

In some embodiments, the process further comprises one or more of the following steps: i) washing the benzalkonium heparinate with water prior to dissolving it in $CH_2Cl_2$; ii) drying the benzalkonium heparinate prior to dissolving it in $CH_2Cl_2$; iii) dissolving the crude LMWH in water and adding methanol to that solution to reprecipitated LMWH; iv) dissolving the reprecipitated LMWH in water and treating it with 0.09-0.07 L of $H_2O_2$ solution (about 33% w/v in water) per Kg of reprecipitated LMWH at a temperature of at least 35-45° C. or 38 42° C. for a period of at least three hours, then neutralizing the solution with acid (e.g. mineral acid aqueous solution) to a pH in the range of about 6-7.5, and adding methanol to achieve a methanol content in the range of about 60-80% relative to the water solution to form oxidized LMWH; v) dissolving the oxidized LMWH in water and treating it with 0.06-0.04 L or 0.055-0.045 L of $H_2O_2$ solution (about 33% w/v in water).

Particular and preferred embodiments for the low molecular weight heparin are as previously defined herein.

In a particular embodiment, the aqueous heparin sodium solution of step a) is prepared from heparin obtained from pig intestinal mucosa. The preferred grade of heparin sodium starting material is as defined in the European Pharmacopoeia or the US Pharmacopoeia.

The addition of quaternary ammonium hydroxide, e.g. Triton B, in step c) can be done by one or several sequential additions, for example by 1, 2, 3 or 4 sequential additions of Triton B. In a specific embodiment, the addition of Triton B in step c) is performed in a maximum of three sequential additions, i.e. 1, 2 or 3, in each one of them adding Triton B in a weight ratio of 0.2:1 to 0.3:1 Triton B:benzalkonium heparinate. Preferably, the addition of Triton B in step c) is performed by three sequential additions of Triton B, and preferably each with the addition of Triton B in a weight ratio of 0.2:1 to 0.3:1 of Triton B:benzalkonium heparinate.

In one embodiment of the invention, the addition of Triton B in step c) is performed by three sequential additions of Triton B, such that after the first addition the reaction is conducted for 6-10 hours before the second portion is added. After the second addition, the reaction is conducted for 12-20 hours before the third portion is added, and after the third addition, the reaction is conducted for 6-10 hours. In a further embodiment, after the first the first portion is added, the reaction is conducted for 7-9 hours before the second portion is added. After the second addition, the reaction is conducted for 14-18 hours before the third portion is added, and after the third addition, the reaction is conducted for 7-9 hours. In yet another embodiment, the reaction time after each of the first, second and third addition is about 8 hours, about 16 hours, and about 8 hours, respectively.

In one embodiment, the temperature in step c) is between 25 and 35° C., preferably between 27 and 32° C.

In a preferred embodiment, the treatment with $H_2O_2$ in step d) is carried out in an aqueous solution of the depolymerized heparin.

Preferably, each treatment with $H_2O_2$ in step d) is performed with a ratio of between 0.04 and 0.5 liters of $H_2O_2$ at 33% w/v per kg of depolymerized heparin, preferably between 0.04 and 0.3 liters of $H_2O_2$ at 33% w/v per kg of depolymerized heparin. In a particular embodiment, each treatment with $H_2O_2$ in stage d) is performed with a ratio between 0.04 and 0.2 liters of $H_2O_2$ at 33% w/v per kg of depolymerized heparin. In a preferred embodiment, step d) comprises a first treatment with $H_2O_2$ of the depolymerized heparin obtained after step c) with a ratio between 0.05 and 0.25 liters of $H_2O_2$ at 33% w/v per kg of depolymerized heparin, and a second treatment with $H_2O_2$ with a ratio of between 0.04 and 0.25 liters of $H_2O_2$ at 33% w/v per kg of depolymerized heparin.

In another embodiment, step d) includes three treatments with $H_2O_2$.

Preferably, step d) is carried out at a temperature of between 2° and 50° C., preferably between 25 and 45° C.

Preferably, each treatment with $H_2O_2$ is performed for at least 3 hours. For example, for between 3 and 20 hours. In a particular embodiment, the first treatment with $H_2O_2$ is performed for a time of between 12 and 20 h, preferably between 14 and 18 h. Preferably, the second and subsequent treatments with $H_2O_2$ are performed for a time of between 3 and 7 h, preferably between 4 and 6 h.

In a preferred embodiment, step d) is carried out at a pH between 10.5 and 11.5. Additionally, the method of the invention may include an additional step of precipitation of the LMWH with a solution of sodium acetate in methanol after each treatment with $H_2O_2$ in step d). In some embodiments, the precipitation of the LMWH is conducted after the first treatment with $H_2O_2$. In a particular embodiment, two treatments with $H_2O_2$ are carried out and a sodium acetate+methanol precipitation step of the LMWH is carried out between the two treatments with $H_2O_2$. In another embodiment, three treatments with $H_2O_2$ are carried out and a sodium acetate+methanol precipitation step of the LMWH is performed between the first and second treatments with $H_2O_2$ and optionally between the second and third treatments with $H_2O_2$.

Preferably, after the first treatment with $H_2O_2$ in step d) the LMWH is precipitated in a solution of sodium acetate in methanol.

In a preferred embodiment, the LMWH obtained with the method of the invention is purified by precipitation with a solution of acetate in methanol.

The LMWH obtained can be subjected to lyophilization and provided as a lyophilized solid.

Another aspect of the invention provides methods of treating conditions that are therapeutically responsive to LMWH by administering the LMWH as defined herein. Exemplary therapeutically responsive conditions that are treated or prevented with the LMWH include prevention of blood clots, treatment of blood clots, treatment of heart attack, treatment of venous thromboembolism (such as deep vein thrombosis and pulmonary embolism), prevention of venous thromboembolism, treatment of myocardial infarction, or treatment of acute coronary syndrome. The method of the invention comprises administering to a subject in need thereof a therapeutically effective or prophylactically effective amount of the composition. The LMWH is preferably administered subcutaneously (sc) or via intravenous (iv) bolus.

Exemplary doses include about 20-50 mg sc once daily, about 30 mg sc once daily, about 0.5-1.5 mg/Kg bodyweight sc one daily, about 1 mg/Kg bodyweight sc one daily, about 25-35 mg single iv bolus plus about 1 mg/Kg sc followed by about 1 mg/Kg sc once daily, about 30 mg single iv bolus plus about 1 mg/Kg sc followed by about 1 mg/Kg sc once daily, about 0.5-1 mg/Kg bodyweight sc every 12 h, about 0.75 mg/Kg bodyweight sc every 12 h, about 40 mg sc once daily for up to 12 days, or about 30 mg sc every 12 h for up to 14 days. Exemplary doses also include about 5000-1000 IU sc once daily, about 115 IU/Kg bodyweight sc once daily, about 2000-5000 IU sc once daily, about 2500 IU sc once daily, about 3000 IU sc once daily, about 3500 IU sc once daily, about 5000 IU sc once daily, about 7500 IU sc once daily, or 10000 about IU sc once daily. Aspirin can also be administered to a subject receiving the LMWH.

The LMWH of the invention can be included in any pharmaceutically acceptable pharmaceutical composition including, by way of example, those described herein and those known to be suitable for administration of LMWH. The pharmaceutical composition comprises LMWH and at least one pharmaceutical excipient. The LMWH can be present in the dosage form as a solid or liquid. The composition may also be included in a vial, ampoule, syringe, bag, bottle or other recognized pharmaceutically acceptable container.

The invention includes all combinations of two or more of the embodiments disclosed herein.

DETAILED DESCRIPTION OF THE INVENTION

Figure 1:
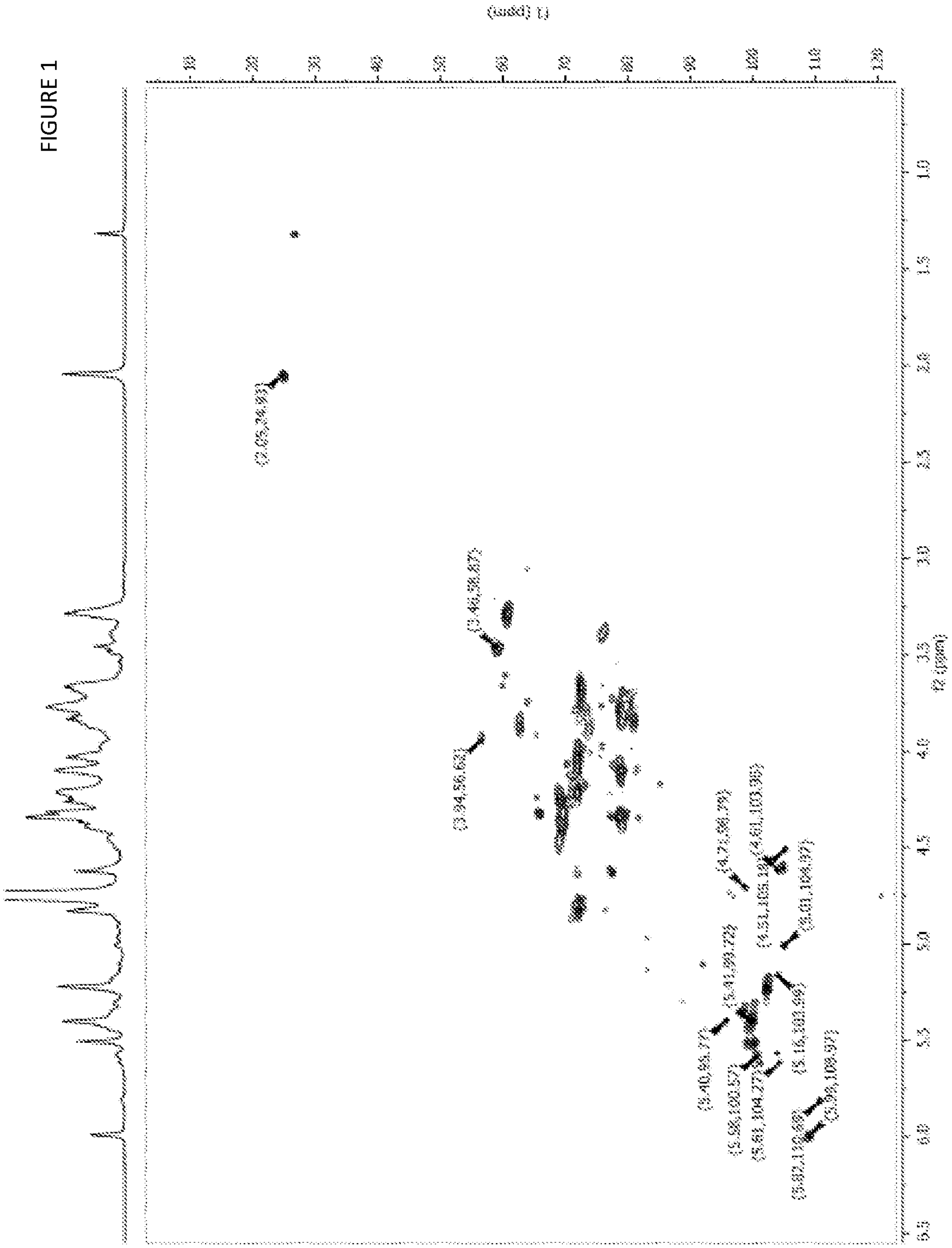
FIG. 1. $^{1}$H NMR spectrum of LMWH obtained by the method of the invention with anomeric zone expansion.

The term "ambient temperature" refers to a temperature in the range of about 20-25° C. or about 20-22° C.

As used herein, the term "approximately" or "about" means±10% or ±5% relative to the given value. For example, 20% w/v±10% is taken to mean 18-22% w/v.

The definitions and embodiments described for one aspect apply equally to all other aspects of the invention.

In the present invention "low molecular weight heparin" or "LMWH" is understood as defined in the document "Heparins, Low-Molecular-Mass monograph, 0828, European Pharmacopeia 9th Ed.", as the polysaccharide mixture obtained from heparin and having an average molecular weight of less than 8,000 Dalton and where at least 60% of its total mass has a molecular weight of less than 8,000 Da. The average molecular weight of the LMWH of the invention has been determined by the method of the European Pharmacopeia (Ph. Eur. 9th Ed.).

In the present invention "1,6-anhydro residues" is understood as various chemical groups that are generated at the terminal positions of the LMWHs during the depolymerization process. Non-limiting examples of these groups are 2-sulfo-amino-1,6-anhydro-2-deoxy-β-D-glucopyranose (1,6-anhydroglucosamine) and 2-sulfo-amino-1,6-anhydro-2-deoxy-β-D-mannopyranose (1,6-anhydromannosamine). The amount of these residues in the LMWH is expressed as the percentage of oligosaccharide chains that have these types of residues at their reducing terminus.

The 1,6-anhydro-terminal content of LMWH can be obtained by the analytical method described in the Enoxaparin Sodium monograph, 1097, European Pharmacopeia 9th Ed, described under Identification B. In this method, the molecule is extensively depolymerized with a mixture of heparinases I, II and III, and the residues generated are separated and quantified by strong anion exchange chromatography (SAX-HPLC). The 1,6-anhydro content, for example, is determined according to the following formula:

$$\%\ 1,6\text{-anhydro} = Mw\cdot(A_1 + A_2 + A_3)\cdot 100/\sum Mw_x\cdot A_x$$

where:

Mw, average molecular weight $MW_x$, molecular weight of derivative x (see table 1097-1 of Enoxaparin Sodium monograph, 1097, European Pharmacopeia 9th Ed)

$A_x$, peak area of derivative x $A_1$, peak area of the 1,6-anhydro derivative ΔIS $A_2$, peak area of 1,6-anhydro derivative ΔIIS $A_3$, peak area of the 1,6-anhydro ΔIS-IS derivative.

The ratio of 1,6-anhydroglucosamine and 1,6-anhydromannosamine residues in LMWH can be determined by Nuclear Magnetic Resonance (NMR), e.g. by $^{1}$H $^{13}$C HSQC. The ratio between the two residues can be determined by integrating the signals corresponding to each of these residues in the spectrum of $^{1}$H $^{13}$C HSQC.

The anti-FXa and anti-FIIa activity of the LMWH of the invention has been determined by the chromogenic method of the European Pharmacopoeia (Ph. Eur. 9th Edition, Monograph 0828) and expressed in international units per mg.

The degree of coloration of LMWH can be determined according to method II of the European Pharmacopoeia chapter 2.2.2.

The LMWH of the invention possesses an advantageous combination of physicochemical properties that ultimately result in a LMWH exhibiting improved stability, improved activity, and improved chemical composition.

The LMWH is prepared according to one or more of the processes described herein, a key aspect of which is the manner in which the depolymerized heparin is treated with hydrogen peroxide solution.

The concentration of benzalkonium heparinate in the solution in which both depolymerization and the first treatment with hydrogen peroxide are carried out can be 20% w/v±2%, i.e. 18-22% w/v) in this and all other examples, unless otherwise indicated. The amount of hydrogen peroxide added at the different stages is equivalent to referencing both benzalkonium heparinate and depolymerized heparin, since after the different additions of Triton B the benzalkonium heparinate present in the reaction depolymerizes, giving rise to depolymerized heparin.

The LMWH has the advantage of being stable at room temperature for 24-36 months and has a degree of coloration≥6 measured with a LICO® brand colorimeter that relates the color according to the reference chromatic range established in Pharmacopoeia (Ph. Eur. (2.2.2, Method II)).

Examples 1-9 below are exemplary of the process and LMWH of the invention. Example 10 exemplifies a process not according to the invention, wherein the process excludes treatment of the depolymerized heparin with hydrogen peroxide, which resulted in an inferior LMWH with an average molecular weight of 3280 Da, an anti-FXa activity of 112 IU/mg and an anti-FIIa activity of 13.70 IU/mg, an 1,6-anhydro residue content of 18.5% at the reducing terminus of its oligosaccharide chains, a degree of coloration of 4, and a shelf-life stability of no more than 9 months at room temperature.

The comparative Example 11 exemplifies another process not according to the invention, wherein the depolymerization is conducted at 60° C. but wherein the depolymerized heparin is otherwise treated with hydrogen peroxide, unlike Example 10. The process resulted in an inferior LMWH having an average molecular weight of 2341 Da, an anti-FXa activity of 109 IU/mg, an anti-FIIa activity of 2.8 IU/mg, a reducing terminus of its oligosaccharide chains a 1,6-anhydro-residue content of 21%, wherein the proportion of 1,6-anhydroglucosamine residues is much lower than that of 1,6-anhydromannosamine residues. The product also exhibited a color grade of 4 and a shelf-life stability of no more than 10-11 months at room temperature. The product required cold storage in order for the product to exhibit stability for more than 12 months.

The LMWH products from Examples 1-11 were analyzed (Example 12) to determine their average molecular weight and percentage of 1,6-anhydro residue content. The data demonstrate that the two comparative processes (Examples 10-11) were unable to provide LMWH having the combination of average molecular weight and 1,6-anhydro residue content as provided by the process of the invention nor were the inferior LMWHs as stable as the improved LMWH provided by the instant process and defined as set forth herein.

The LMWH products from Examples 1-11 were analyzed (Examples 13-14) to determine their NMR spectra and thereby obtain their respective residue content of 2-sulfo-amino-1,6-anhydro-2-deoxy-β-D-glucopyranose (1,6-anhydroglucosamine or 1,6-an.A), 2-sulfo-amino-1,6-anhydro-2-deoxy-β-D-mannopyranose (1,6-anhydromannosamine or 1,6-an.M), 1,6-anhydromannosamine and 1,6-anhydroglucosamine. The data indicate that the two comparative processes (Example 10-11) were unable to provide LMWH having the target molar ratio of 1.6-an.A/1.6-an.M, because the inferior LMWHs of Examples 10-11 had a ratio of 0.85 or 0.82, respectively.

In order to further establish the improvement of the instant process and LMWH, the process described in EP 1070503 was reproduced (Example 15) in two ways: one wherein the process was conducted as described in the '503 patent and another wherein the improvement of the instant process (the manner in which the hydrogen peroxide treatment is conducted) was added to the prior art process. Accordingly, depolymerization of the heparin with Triton B was conducted with two stages of treatment with hydrogen peroxide at pH between 10.5 and 11.5, in the first stage adding 0.08 liters of $H_2O_2$ 33% w/v per kg of benzalkonium heparinate at a temperature of 40±2° C. (5 hours of reaction) and in the second stage adding 0.05 liters of $H_2O_2$ 33% w/v per kg of benzalkonium heparinate at a temperature of 40° C.±2° C. for about 5 hours. The inferior LMWH made according to the prior art process exhibited a content of 1,6-anhydromannosamine residues greater than the content of 1,6-anhydroglucosamine residues and exhibited a coloration of 4. In contrast, when the prior process was modified according to the invention, the improved LMWH exhibited a content of 1,6-anhydromannosamine residues less than the content of 1,6-anhydroglucosamine residues and exhibited a coloration of ≥6.

The impact of the ratio of hydrogen peroxide to benzalkonium heparinate and of the period of treatment upon the characteristics of the resulting LMWH were evaluated according to Example 16. In each case, the resulting improved LMWH exhibited the target combination of properties.

A dosage form can be made by any conventional means known in the pharmaceutical industry. A liquid dosage form can be prepared by providing at least one liquid carrier and LMWH composition in a container. One or more other excipients can be included in the liquid dosage form. A solid dosage form can be prepared by providing at least one solid carrier and LMWH composition. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container suitable for use with LMWH compositions.

The composition of the invention can be included in any dosage form. Particular dosage forms include a solid or liquid dosage forms.

Finished product can be included in Type I glass pre-filled syringes with chlorobutyl rubber stopper fitted with injection needle and an automatic safety device for some presentations. The needle shield can be made of synthetic rubber and a rigid cover of polypropylene. Primary packaging components can include: sySyringe barrel type I glass of European Pharmacopoeia quality, plunger stopper, type I chlorobutyl rubber stopper of European Pharmacopoeia quality, functional secondary packaging components, plunger rod, automatic safety system (optional or as needed).

The content of oxygen in an aqueous liquid (e.g. water for injection) containing the LMWH is controlled or kept to a minimum so as to reduce or prevent the LMWH injection solution from becoming colored during storage. The oxygen content is measured with an oximeter. The oxygen content in the solution is preferably no more than about 0.5 ppm or no more than about 0.3 ppm.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals.

Exemplary solvents are listed as class 2 or class 3 solvents. Class 3 solvents include, for example, acetic acid, acetone, anisole, 1-butanol, 2-butanol, butyl acetate, tert-butylmethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

Although not necessary, the composition or formulation may further comprise one or more chelating agents, one or more preservatives, one or more antioxidants, one or more adsorbents, one or more acidifying agents, one or more alkalizing agents, one or more antifoaming agents, one or more buffering agents, one or more colorants, one or more electrolytes, one or more salts, one or more stabilizers, one or more tonicity modifiers, one or more diluents, or a combination thereof.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

As used herein, the term "about" is intended to mean±20%, ±15%, ±10%, ±5%, ±2.5% or ±1% relative to a specified value, i.e. "about 20%" means 20±2%, 20±1%, 20±0.5% or 20±0.25%.

EXAMPLES

The following specific examples are provided to illustrate the nature of the present invention. These examples are included for purposes of illustration only and should not be understood as limiting the invention claimed herein.

Example 1

10 g of sodium heparin is dissolved in purified water and under agitation a 50% (w/v) solution of benzalkonium chloride is added, thereby forming benzalkonium heparinate, which is separated from the water such as by filtration or centrifugation. The heparinate product formed is washed several times with water to remove excess chlorides and finally the product is dried by lyophilization.

Benzalkonium heparinate is dissolved in methylene chloride and the temperature is adjusted to 30±5° C. Benzyltrimethylammonium hydroxide (Triton B) (40% w/v in methanol) is added at a weight ratio of 0.25:1 Triton B:benzalkonium heparinate and allowed to react at the above-specified temperature for about 8 hours. The addition of Triton B (at the same weight ratio) is repeated two more times: a) one addition that is left to react for about 16 hours at the above-specified temperature and a subsequent addition that is left to react for about 8 hours at the above-specified temperature.

$H_2O_2$ (33% w/v in water) is added to the solution of the depolymerized product, at a pH in the range of about 10.5-11.5; specifically, 0.1 liter±10% of the $H_2O_2$ solution are added per kg of benzalkonium heparinate, and the reaction mixture is left to react at 30±5° C. for more than 3 hours (preferably about 14-18 hours). After the target reaction time is achieved, product is precipitated over a solution of sodium acetate (about 15-20% or about 17% w/v in methanol) by adding the heparinate solution to the sodium acetate solution such that the concentration of methanol in the final mixture with water is about 60-80% w/v, thereby forming solidified crude LMWH sodium salt in the solution. The crude LMWH sodium salt is then isolated by centrifugation.

This crude low molecular weight heparin sodium salt is then dissolved in water and precipitated again with sodium acetate in methanol as above. The LMWH sodium salt precipitate is again dissolved in purified water and treated with $H_2O_2$ solution as above, specifically, 0.08 liters±10% of the $H_2O_2$ per kg of benzalkonium heparinate (relative to the benzalkonium heparinate formed at the beginning of the process) is added at a temperature of 40±2° C. and allowed to react for more than 3 hours (preferably about 5 hours). After the reaction period, the solution is neutralized with aqueous HCl (5 N) to a pH of about 6-7.5. The LMWH sodium is precipitated again with sodium acetate in methanol as above. The precipitated LMWH sodium salt is again isolated by centrifugation.

The LMWH sodium salt precipitate is redissolved in purified water and treated again with 0.05±10% liters of $H_2O_2$ solution per kg benzalkonium heparinate (again, relative to the benzalkonium heparinate formed at the beginning of the process) at a temperature of 40° C.±2° C. for more than 3 hours (about 5 hours). After the reaction period, the solution is neutralized with acid as above and precipitated with sodium acetate in methanol as above.

The purified product is dissolved in water and lyophilized, yielding 6.00 g of low molecular weight heparin with an average molecular weight of 3241 Da, an anti-FXa activity of 118 IU/mg, and an anti-FIIa activity of 13.7 IU/mg. The content of 1,6-anhydro residues in the reducing terminal of its oligosaccharide chains is in the range of about 1-15% where the proportion of 1,6-anhydroglucosamine residues is greater or equal to that of 1,6-anhydromannosamine residues, unlike other low molecular weight heparins of the prior art.

This low molecular weight heparin also has the advantage of being stable at room temperature for 24-36 months and has a degree of coloration≥6 measured with a LICO® brand colorimeter that relates the color according to the reference chromatic range established in Pharmacopoeia (Ph. Eur. (2.2.2, Method II)).

The degree of coloration, a parameter directly related to the stability of the product, was used to determine that the final packaged product was stable at room temperature for between 24 and 36 months. The final package product is placed in one or more sealed polyethylene bags which are then placed into an aluminum drum with an aluminum cover.

Example 2

Starting from 10 g of sodium heparin and repeating the steps indicated in Example 1, Low molecular weight heparin (6.01 g) with an average molecular weight of 3259 Da, an anti-FXa activity of 103 IU/mg, and an anti-FIIa activity of 15.2 IU/mg are obtained. This low molecular weight heparin presents the characteristic of having in the reducing terminal end of its oligosaccharide chains a content of 1,6-anhydro residues between 1 and 15%, where the proportion of 1,6-anhydroglucosamine residues is higher than that of 1,6-anhydromannosamine residues, unlike other low molecular weight heparins.

This low molecular weight heparin also has the advantage of being stable at room temperature for 24-36 months, presenting a color grade≥6 measured with a LICO® brand colorimeter that establishes the color according to the reference chromatic range established in Pharmacopoeia (Ph. Eur. (2.2.2, Method II)).

The degree of coloration, a parameter directly related to the stability of the product, made it possible to determine that the final packaged product was stable at room temperature for between 24 and 36 months.

Example 3

10 g of sodium heparin is dissolved in purified water and under agitation a 50% (w/v) solution of benzalkonium chloride is added, forming benzalkonium heparinate. The product formed is washed several times with water to remove excess chlorides and finally the product is dried by lyophilization.

Benzalkonium heparinate is dissolved in methylene chloride and the temperature is adjusted to 30° C.±5° C. Benzyltrimethylammonium hydroxide (Triton B) is added at 40% w/v in methanol at a weight ratio of 0.25:1 Triton B:benzalkonium heparinate and allowed to react at the above temperature. The addition is repeated two more times, leaving the first addition of Triton B for 8 hours, the second for 16 hours, and the third for another 8 hours.

$H_2O$ 2 at 33% w/v is added to the solution of the depolymerized product, at a pH between 10.5 and 11.5; specifically, 0.1±10% liters of $H_2O_2$ at 33% w/v/kg of benzalkonium heparinate (relative to the benzalkonium heparinate formed above), and it is left to react at 30±5° C. for 16 hours. After the reaction time, it is precipitated over a solution of sodium acetate in methanol and the crude low molecular weight heparin is isolated by centrifugation.

This crude low molecular weight heparin is dissolved in water and precipitated again with sodium acetate in methanol. The precipitate is dissolved in purified water and treated with $H_2O_2$ 33% w/v; specifically, 0.08±10% liters of $H_2O_2$ 33% w/v/kg of benzalkonium heparinate (relative to the benzalkonium heparinate formed above) is added at a temperature of 40±2° C. After 5 hours of reaction, the solution is neutralized and precipitated with sodium acetate in methanol.

The purified product is dissolved in water and lyophilized, yielding 5.21 g of low molecular weight heparin with an average molecular weight of 3269 Da, an anti-FXa activity of 119 IU/mg and an anti-FIIa activity of 13.70 IU/mg and presents in the reducing terminal of its oligosaccharide chains a content of 1,6-anhydro residues between 1 and 15%, where the proportion of 1,6-anhydroglucosamine residues is higher or equivalent to that of 1,6-anhydromannosamine residues, unlike other low molecular weight heparins.

This low molecular weight heparin also has the advantage of being stable at room temperature for 24-36 months, presenting a degree of coloration≥6 measured with a LICO® brand colorimeter that relates the color according to the reference chromatic range established in Pharmacopoeia (Ph. Eur. (2.2.2, Method II)).

The color grade, a parameter directly related to the stability of the product, made it possible to determine that the final packaged product was stable at room temperature for between 24 and 36 months.

Example 4

Starting from 10 g of heparin sodium and repeating the steps indicated in Example 1, 6.25 g of low molecular weight heparin with an average molecular weight of 3172 Da, an anti-FXa activity of 108 IU/mg and an anti-FIIa activity of 13.1 IU/mg and a residue profile of 1,6-anhydro at the reducing terminus of its oligosaccharide chains between 1 and 15%, where the proportion of 1,6-anhydroglucosamine residues is higher or equivalent to that of 1,6-anhydromannosamine residues, unlike other low molecular weight heparins such as enoxaparin.

This low molecular weight heparin also has the advantage of being stable at room temperature for 24-36 months, presenting a degree of coloration≥6 measured with a LICO® brand colorimeter that relates the color according to the reference chromatic range established in Pharmacopoeia (Ph. Eur. (2.2.2, Method II)).

The color grade, a parameter directly related to the stability of the product, made it possible to determine that the final packaged product was stable at room temperature for between 24 and 36 months.

Example 5

Starting from 10 g of heparin sodium and repeating the steps indicated in Example 1, 6.34 g of low molecular weight heparin with an average molecular weight of 3347 Da, an anti-FXa activity of 110 IU/mg and an anti-FIIa activity of 14.7 IU/mg and a residue profile of 1,6-anhydro at the reducing terminus of its oligosaccharide chains between 1 and 15%, where the proportion of 1,6-anhydroglucosamine residues is higher or equivalent to that of 1,6-anhydromannosamine residues, unlike other low molecular weight heparins such as enoxaparin.

This low molecular weight heparin also has the advantage of being stable at room temperature for 24-36 months, presenting a color grade≥6 measured with a LICO® brand colorimeter that establishes the color according to the reference chromatic range established in Pharmacopoeia (Ph. Eur. (2.2.2, Method II)). The color grade, a parameter directly related to the stability of the product, made it possible to determine that the final packaged product was stable at room temperature for between 24 and 36 months.

Example 6

Starting from 10 g of heparin sodium and repeating the steps indicated in Example 1, 7.11 g of low molecular weight heparin with an average molecular weight of 3400 Da, an anti-FXa activity of 119 IU/mg and an anti-FIIa activity of 15.0 IU/mg and a residue profile of 1,6-anhydro at the reducing terminus of its oligosaccharide chains between 1 and 15%, where the proportion of 1,6-anhydroglucosamine residues is higher than that of 1,6-anhydromannosamine residues, unlike other low molecular weight heparins such as enoxaparin.

This low molecular weight heparin also has the advantage of being stable at room temperature for 24-36 months, presenting a degree of coloration≥6 measured with a LICO® brand colorimeter that relates the color according to the reference chromatic range established in Pharmacopoeia (Ph. Eur. (2.2.2, Method II)). The color grade, a parameter directly related to the stability of the product, made it possible to determine that the final packaged product was stable at room temperature for between 24 and 36 months.

Example 7

Starting from 10 g of heparin sodium and repeating the steps indicated in Example 1, we obtain 6.92 g of low molecular weight heparin with an average molecular weight of 3328 Da, an anti-FXa activity of 117 IU/mg and an anti-FIIa activity of 14.9 IU/mg and a residue profile of 1,6-anhydro at the reducing terminus of its oligosaccharide chains between 1 and 15%, where the proportion of 1,6-anhydroglucosamine residues is higher or equivalent to that of 1,6-anhydromannosamine residues, unlike other low molecular weight heparins such as enoxaparin.

This low molecular weight heparin also has the advantage of being stable at room temperature for 24-36 months, presenting a color grade≥6 measured with a LICO® brand colorimeter that establishes the color according to the reference chromatic range established in Pharmacopoeia (Ph. Eur. (2.2.2, Method II)). The degree of color, a parameter directly related to the stability of the product, made it possible to determine that the final packaged product was stable in an interval between 24 and 36 months.

Example 8

Starting from 10 g of heparin sodium and repeating the steps indicated in Example 3, 7.04 g of low molecular weight heparin with an average molecular weight of 3331 Da, an anti-FXa activity of 113 IU/mg and an anti-FIIa activity of 15.3 IU/mg and a residue profile of 1,6-anhydro at the reducing terminus of its oligosaccharide chains between 1 and 15%, where the proportion of 1,6-anhydroglucosamine residues is higher or equivalent to that of 1,6-anhydromannosamine residues, unlike other low molecular weight heparins such as enoxaparin.

This low molecular weight heparin also has the advantage of being stable at room temperature for 24-36 months, presenting a color grade≥6 measured with a LICO® brand colorimeter that establishes the color according to the reference chromatic range established in Pharmacopoeia (Ph. Eur. (2.2.2, Method II)). The color grade, a parameter directly related to the stability of the product, made it possible to determine that the final packaged product was stable at room temperature for between 24 and 36 months.

Example 9

Starting from 10 g of heparin sodium and repeating the steps indicated in Example 3, 7.09 g of low molecular weight heparin with an average molecular weight of 3366 Da, an anti-FXa activity of 115 IU/mg and an anti-FIIa activity of 16.0 IU/mg and a residue profile of 1,6-anhydro at the reducing terminus of its oligosaccharide chains between 1 and 15%, where the proportion of 1,6-anhydroglucosamine residues is higher or equivalent to that of 1,6-anhydromannosamine residues, unlike other low molecular weight heparins such as enoxaparin.

This low molecular weight heparin also has the advantage of being stable at room temperature for 24-36 months, presenting a color grade≥6 measured with a LICO® brand colorimeter that establishes the color according to the reference chromatic range established in Pharmacopoeia (Ph. Eur. (2.2.2, Method II)). The color grade, a parameter directly related to the stability of the product, made it possible to determine that the final packaged product was stable at room temperature for between 24 and 36 months.

Comparative Example 10 (No Treatment with $H_2O_2$)

10 g of sodium heparin is dissolved in purified water and under agitation a 50% (w/v) solution of benzalkonium chloride is added, forming benzalkonium heparinate. The product formed is washed several times with water to remove excess chlorides and finally the product is dried by lyophilization.

Benzalkonium heparinate is dissolved in methylene chloride and the temperature is adjusted to 30±5° C. Benzyltrimethylammonium hydroxide (Triton B) is added at 40% w/v in methanol at a weight ratio of 0.25:1 Triton B:benzalkonium heparinate and allowed to react at the above temperature. The addition is repeated two more times, leaving the first addition of Triton B for 8 hours, the second for 16 hours and the third for another 8 hours.

The depolymerized product solution is precipitated over a solution of sodium acetate in methanol, and the crude low molecular weight heparin is isolated by centrifugation.

This crude low molecular weight heparin is dissolved in water and precipitated again with methanol. The precipitate is dissolved in purified water at a temperature of 40±2° C. at pH 11. After 5 hours, the solution is neutralized and precipitated with methanol.

The purified product is dissolved in water and lyophilized, yielding 5.28 g of low molecular weight heparin with an average molecular weight of 3280 Da, an anti-FXa activity of 112 IU/mg and an anti-FIIa activity of 13.70 IU/mg, and has a 1,6-anhydro residue content of 18.5% at the reducing terminus of its oligosaccharide chains.

In addition, the ratio of 1,6-anhydroglucosamine residues to 1,6-anhydromannosamine residues is analyzed; unlike in the previous examples, the content of 1,6-anhydromannosamine residues are greater than the content 1,6-anhydroglucosamine residues.

We also analyzed the degree of stability correlated with the color of the sample, observing that from the tenth month at room temperature it presents a degree of coloration of 4 measured with a LICO® brand colorimeter that establishes the color according to the chromatic range of reference established in Pharmacopoeia (Ph. Eur. (2.2.2, Method II)).

The degree of coloration, a parameter directly related to product stability, made it possible to determine that the final packaged product was not stable for more than 9 months at room temperature, so the additions of $H_2O_2$ seem to be responsible for this behavior.

Comparative Example 11 (Depolymerization at 60° C.)

10 g of sodium heparin is dissolved in purified water and under agitation a 50% (w/v) solution of benzalkonium chloride is added, forming benzalkonium heparinate. The product formed is washed several times with water to remove excess chlorides and finally the product is dried by lyophilization.

Benzalkonium heparinate is dissolved in methylene chloride and the temperature is adjusted to 60±5° C. Benzyltrimethylammonium hydroxide (Triton B) is added at 40% w/v in methanol at a weight ratio of 0.25:1 Triton B:benzalkonium heparinate and allowed to react at the above temperature. The addition is repeated two more times, leaving the first addition of Triton B for 8 hours, the second for 16 hours and the third for another 8 hours.

Hydrogen peroxide at 33% w/v is added to the dissolution of the depolymerized product at a pH between 10.5 and 11.5, specifically 0.1±10% liters of $H_2O_2$ at 33% w/v/kg of benzalkonium heparinate and is left to react at 30±5° C. for 16 hours. After the reaction time, it is precipitated over a solution of sodium acetate in methanol, and the crude low molecular weight heparin is isolated by centrifugation.

This crude low molecular weight heparin is dissolved in water and precipitated again with methanol. The precipitate is dissolved in purified water and treated with hydrogen peroxide at 33% w/v; specifically, 0.08±10% liters of $H_2O_2$ 33% w/v per kg of benzalkonium heparinate is added at a temperature of 40±2° C. After 5 hours of reaction, the solution is neutralized and precipitated with methanol.

The precipitate is dissolved in purified water and treated again with 0.05±10% liters of $H_2O_2$ 33% w/v per kg of benzalkonium heparinate $H_2O_2$ 33% w/v at a temperature of 40° C.±2° C. for about 5 hours. After the reaction period, the solution is neutralized and precipitated with sodium acetate in methanol. The purified product is dissolved in water and lyophilized, yielding 5.10 g of low molecular weight heparin with an average molecular weight of 2341 Da, an anti-FXa activity of 109 IU/mg and an anti-FIIa activity of 2.8 IU/mg and presents in the reducing terminus of its oligosaccharide chains a 1,6-anhydro-residue content of 21%, where the content of 1,6-anhydroglucosamine residues is much lower than that of 1,6-anhydromannosamine residues.

We also analyzed the degree of stability correlated with the color of the sample, observing that from the tenth month at room temperature it presents a color grade of 4 measured with a LICO® brand colorimeter that establishes the color according to the chromatic range of reference established in Pharmacopoeia (Ph. Eur. (2.2.2, Method II)).

The degree of coloration, a parameter directly related to product stability, made it possible to determine that the final packaged product was not stable for more than 10-11 months at room temperature, requiring cold storage (at least refrigeration) for product stability to exceed 12 months.

Example 12

The products obtained in Examples 1 to 11 were analyzed to determine the percentage of 1,6-anhydro residue content in a specific manner according to the method described in Enoxaparin Sodium monograph, 1097, European Pharmacopeia 9th Ed, described under Identification B, yielding the following results.

| Example | Average molecular weight, Da | 1,6-anhydrous content, % |
|---|---|---|
| 1 | 3241 | 8 |
| 2 | 3259 | 9 |
| 3 | 3269 | 11 |
| 4 | 3172 | 8 |
| 5 | 3347 | 7 |
| 6 | 3400 | 5 |
| 7 | 3328 | 5 |
| 8 | 3331 | 4 |
| 9 | 3366 | 4 |
| 10 | 3280 | 18.5 |
| 11 | 2341 | 21 |

Example 13

The product obtained in example 1, is analyzed by nuclear magnetic resonance, specifically by the $^{1}$H-RMN and $^{1}$H-$^{13}$C HSQC experiments.

$^{1}$H-RMN spectroscopy has been the most widely used technique for the study of these compounds since it is an abundant nucleus with a high gyromagnetic ratio. The region between 1.8-2.1 ppm comprises the signals corresponding to the N-acetyl groups or methyl groups of the reducing termini that can be synthetically included. The region between 2.8-4.6 ppm comprises the majority of the saccharide ring signals and has a high degree of overlap between them, making it difficult to extract structural information directly from this area. The signals corresponding to the anomeric protons are in the region between 4.6-6.0 ppm. Since this zone is much less populated with signals, it is possible to extract a great deal of information from it. Furthermore, in the case of LMWHs obtained by β-elimination mechanism, it also contains the signals corresponding to the H4 of the non-reducing termini of the molecule.

Specifically, the signals corresponding to the 1,6-anhydro residues appear at 5.57 and 5.62 ppm, corresponding to the anomeric proton of the 1,6-anhydromannosamine and 1,6-anhydroglucosamine structures, respectively, as described in the literature.

Another two-dimensional experiment of particular importance for the structural characterization of this type of compounds is 1H-13C HSQC (Heteronuclear Single-Quantum Correlation), which correlates proton chemical shifts with carbon-13 chemical shifts and allows assigning the primary structures of oligosaccharides derived from GAGs and the monosaccharide composition.

The increased spectral dispersion achieved with this two-dimensional technique allows the quantification of the integrals of the overlapping signals in the corresponding one-dimensional spectra.

Figure 2:
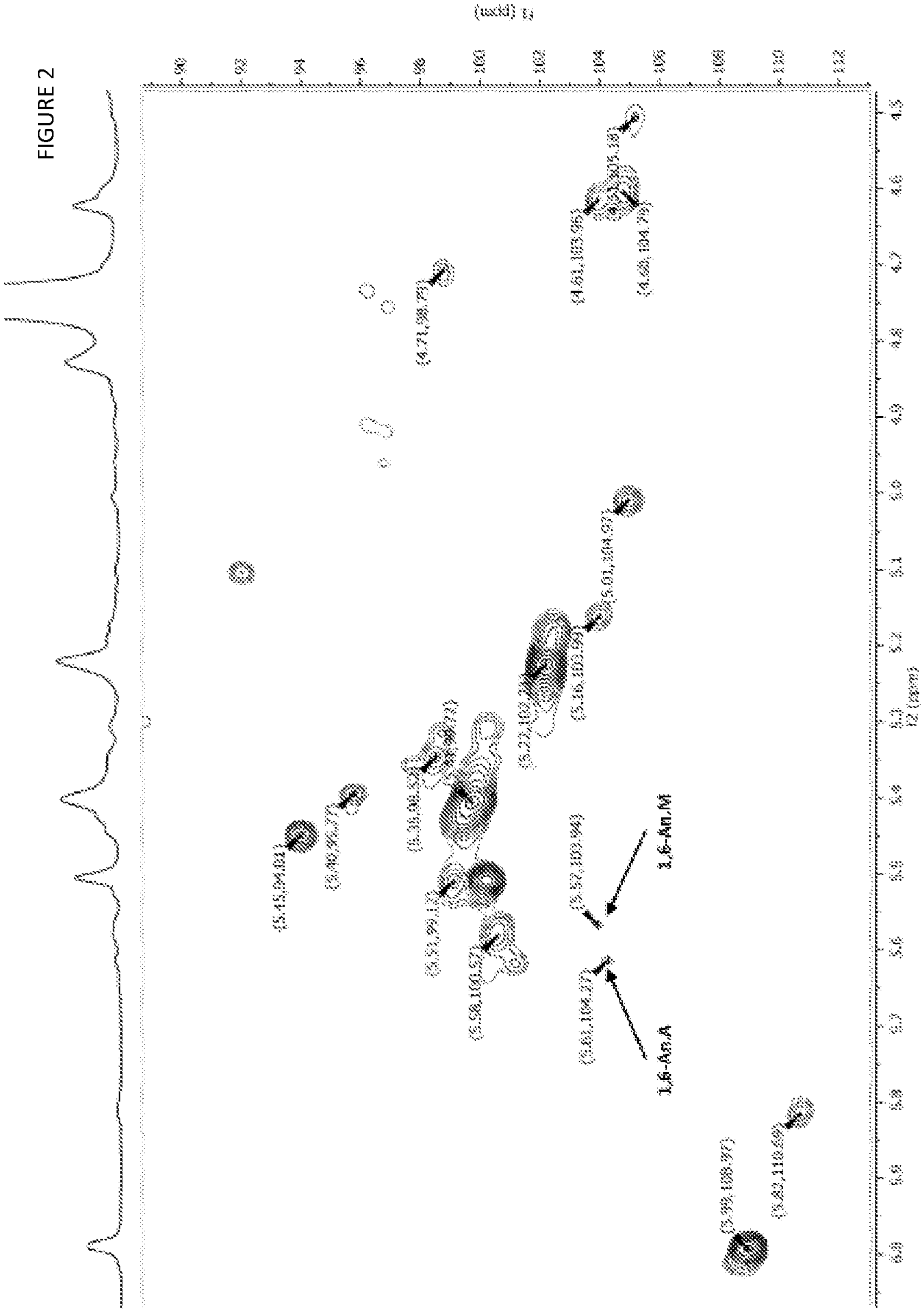
FIG. 2. Spectrum of 1H 13C HSQC of LMWH obtained by the method of the invention with anomeric zone expansion.

The signals corresponding to the 1,6-anhydro residues appear at 5.57-103.9 and 5.61-104.3 ppm, corresponding to the anomeric proton of the 1,6-anhydromannosamine and 1,6-anhydroglucosamine structures, respectively, as described in the literature and as observed in FIGS. 1 and 2 for the product sample obtained in Example 1.

Example 14

The products obtained in examples 1 to 11 were analyzed for the residue content of 2-sulfo-amino-1,6-anhydro-2-deoxy-β-D-glucopyranose (1,6-anhydroglucosamine or 1,6-an.A) and 2-sulfo-amino-1,6-anhydro-2-deoxy-β-D-mannopyranose (1,6-anhydromannosamine or 1,6-an.M), according to the method known in the state of the art for 1H-13C HSQC experiments, obtaining the following results.

| Example | 1,6-an.A, % mol. | 1,6-an. M, % mol. | Ratio 1.6-an.A/1.6-an.M (relative ratio) |
|---|---|---|---|
| 1 | 0.61 | 0.54 | 1.13 |
| 2 | 0.74 | 0.62 | 1.19 |
| 3 | 0.97 | 0.88 | 1.10 |
| 4 | 0.66 | 0.50 | 1.31 |
| 5 | 0.51 | 0.38 | 2.13 |
| 6 | 0.26 | 0.23 | 1.13 |
| 7 | 0.25 | 0.20 | 1.25 |
| 8 | 0.16 | 0.08 | 2.00 |

-continued

| Example | 1,6-an.A, % mol. | 1,6-an. M, % mol. | Ratio 1.6-an.A/1.6-an.M (relative ratio) |
|---|---|---|---|
| 9 | 0.17 | 0.16 | 1.06 |
| 10 | 1.21 | 1.43 | 0.85 |
| 11 | 1.40 | 1.70 | 0.82 |

Example 15: Reproduction of Example 1 of EP1070503 and of the Same Example with the Addition of the Hydrogen Peroxide Treatments Example 1 described in EP1070503 was reproduced as described therein and then with the following exception: adding, after depolymerization with Triton B, two stages of treatment with hydrogen peroxide at pH between 10.5 and 11.5, in the first stage adding 0.08 liters of $H_2O_2$ 33% w/v per kg of benzalkonium heparinate at a temperature of 40±2° C. (5 hours of reaction) and in the second stage adding 0.05 liters of $H_2O_2$ 33% w/v per kg of benzalkonium heparinate (formed above) at a temperature of 40±2° C. for about 5 hours.

By reproducing Example 1 of EP1070503, a low molecular weight heparin was obtained which presented at the reducing terminus of its oligosaccharide chains a 1,6-anhydro residue content of 0.3%, whereas when the two hydrogen peroxide treatment steps described above were added this content was 6%. Furthermore, the 1,6-anhydromannosamine residues are higher than the 1,6-anhydroglucosamine residues when reproducing Example 1 of EP1070503, while when performing the hydrogen peroxide treatments described above the molar content of the 1,6-anhydroglucosamine residues was greater than or equal to that of the 1,6-anhydromannosamine residues.

When reproducing example 1 of EP1070503 and analyzing the degree of stability correlated with the color of the sample, it was observed that from the tenth month at room temperature it presents a degree of coloration of 4 measured with a LICO® brand colorimeter that relates the color according to the reference chromatic range established in Pharmacopoeia (Ph. Eur. (2.2.2, Method II)). However, when the prior art process was modified according to the invention with the peroxide treatments described above, the product obtained proved to be stable at room temperature for 24-36 months presenting a degree of coloration≥6 measured with a LICO® brand colorimeter that relates the color according to the reference chromatic range established in Pharmacopoeia (Ph. Eur. (2.2.2, Method II)).

Example 16

Examples 1 and 3 were repeated varying the amounts of hydrogen peroxide added, which always ranged in each treatment between 0.04 and 1.0 liters of $H_2O_2$ 33% w/v/kg benzalkonium heparinate (or depolymerized heparin) and for times between 3 and 20 hours.

| First treatment* | Second treatment* | Third treatment* |
|---|---|---|
| 0.2 for 3 hours | 0.2 for 3 hours | — |
| 0.3 for 3 hours | 0.3 for 3 hours | — |
| 0.5 for 3 hours | 0.5 for 3 hours | — |
| 0.6 for 3 hours | 0.6 for 3 hours | — |
| 0.8 for 3 hours | 0.8 for 3 hours | — |
| 0.04 for 20 hours | 0.04 for 20 hours | 0.04 for 20 hours |

-continued

| First treatment* | Second treatment* | Third treatment* |
|---|---|---|
| 0.08 for 18 hours | 0.08 for 7 hours | 0.08 for 7 hours |
| 0.1 for 16 hours | 0.1 for 5 hours | 0.1 for 5 hours |
| 0.25 for 14 hours | 0.25 for 4 hours | 0.25 for 4 hours |
| 0.1 for 16 hours | 0.08 for 5 hours | 0.05 for 5 hours |
| 0.04 for 18 hours | 0.05 for 7 hours | — |

*liters of $H_2O_2$ 33% w/v/kg benzalkonium heparinate

In all cases, the heparins obtained had an average molecular weight of between 3 and 3.8 KDa, an anti-FXa activity of between 80-120 IU/mg and an anti-FIIa activity of between 5-20 IU/mg.

Likewise, in all cases the heparins obtained presented in the reducing terminus of their oligosaccharide chains a content of 1,6-anhydro residues ranging from 1 to 15%, and the content of the 1,6-anhydroglucosamine residues was greater than or equal to that of the 1,6-anhydromannosamine residues.

Example 17

The LMWH is administered as liquid via subcutaneous injection or intravenous bolus to a subject in need thereof. The LMWH (30 mg) is dissolved in sterile water and administered to the subject.

The invention claimed is:

1. A low molecular weight heparin (LMWH) exhibiting a 1,6-anhydro residue content of about 1-15% at the reducing terminus of its oligosaccharide chains, a weight average molecular weight in the range of about 3-3.8 KDa, and a molar ratio of 1,6-anhydroglucosamine residues: 1,6 anhydromannosamine residues that is greater than or equal to about 1:1, wherein the LMWH has been prepared according to a process comprising the step of treating quaternary ammonium hydroxide depolymerized heparin salt with about 0.04-1 L of $H_2O_2$, which is about 30-35% w/v in water, per Kg of heparin salt, wherein the quaternary ammonium hydroxide depolymerized heparin has been prepared by three treatments of benzalkonium heparin salt, each with a portion of methanol solution of quaternary ammonium hydroxide at a temperature of 30±5° C.

2. A pharmaceutical composition comprising a LMWH according to claim 1 and at least one pharmaceutical excipient.

3. The LMWH of claim 1, wherein said treating quaternary ammonium hydroxide depolymerized heparin salt with about 0.04-1 L of $H_2O_2$ is conducted at a temperature of about 20-50° C. for a period of at least 3 h.

4. The LMWH of claim 1, wherein the process further comprises one or more of the following steps: a) prior to the step of treating quaternary ammonium hydroxide depolymerized heparin salt with about 0.04-1 L of $H_2O_2$, preparing an aqueous solution of heparin sodium, adding benzalkonium chloride to said solution to form benzalkonium heparinate, dissolving said benzalkonium heparinate in $CH_2Cl_2$, and adding benzyltrimethylammonium hydroxide to the dissolved benzalkonium heparinate, thereby forming said quaternary ammonium hydroxide depolymerized benzalkonium heparin salt; b) after completion of the treating quaternary ammonium hydroxide depolymerized heparin salt with about 0.04-1 L of $H_2O_2$ step(s), adding a solution of sodium acetate in methanol, thereby precipitating the LMWH as LMWH sodium salt; c) lyophilizing a solution comprising the LMWH, thereby forming lyophilized LMWH; d) purifying the LMWH by way of a precipitation with a solution of sodium acetate in methanol, thereby forming LMWH sodium salt; e) forming a heparin salt and depolymerizing said salt to form said depolymerized heparin salt; and/or f) isolating said LMWH as a LMWH salt.

5. The LMWH of claim 4, wherein the process further comprises one or more of the following steps: i) washing the benzalkonium heparinate with water prior to dissolving it in $CH_2Cl_2$; ii) drying the benzalkonium heparinate prior to dissolving it in $CH_2Cl_2$; iii) dissolving the LMWH sodium salt in water and adding a solution of sodium acetate in methanol to form reprecipitated LMWH sodium salt.

6. The LMWH of claim 4, wherein a) the mixture of benzalkonium heparinate, $CH_2Cl_2$, and benzyltrimethylammonium hydroxide is maintained at a temperature of about 20-40° C. for a period of about 8 h or more; b) the treating quaternary ammonium hydroxide depolymerized heparin salt with about 0.04-1 L of $H_2O_2$ step is conducted in two or more treating substeps by adding respective two or more portions of the $H_2O_2$ solution to the depolymerized heparin and allowing the respective portions to react with the depolymerized heparin for respective periods; c) the treating quaternary ammonium hydroxide depolymerized heparin salt with about 0.04-1 L of $H_2O_2$ step is conducted by sequentially treating the depolymerized benzalkonium heparinate with two or more portions of $H_2O_2$ solution, wherein each portion is allowed to react for about 3 h or more at a temperature of about 20° C. or more before addition of a subsequent portion; d) the treating quaternary ammonium hydroxide depolymerized heparin salt with about 0.04-1 L of $H_2O_2$ step is conducted at pH in the range of about 10.5-11.5; e) the weight ratio of benzyltrimethylammonium hydroxide:benzalkonium heparinate is about 0.2:1 to 0.3:1; f) the benzyltrimethylammonium hydroxide is present at 40% w/v in methanol when being added to the benzalkonium heparinate; and/or g) the benzalkonium heparinate is prepared by treating sodium heparinate in water with a solution of benzalkonium chloride (50% w/v) in water at a temperature in the range of about 25-35° C.

7. The LMWH of claim 4, wherein i) the concentration of heparin sodium in the solution of step a) is in the range of about 10-15% w/v; ii) the benzalkonium chloride is present as an about 50% w/v aqueous solution that is added to the solution of heparin sodium of step a); iii) the concentration of benzalkonium heparinate in the $CH_2Cl_2$ is in the range of about 20-30% w/v); iv) the weight ratio of benzyltrimethylammonium hydroxide to benzalkonium heparinate is in the range of about 0.2:1 to 0.3:1; v) the benzyltrimethylammonium hydroxide is present as an about 35-45% or about 40% w/v in methanol prior to addition to the benzalkonium heparinate in the $CH_2Cl_2$; vi) the benzyltrimethylammonium hydroxide is added in at least two portions; vii) the benzyltrimethylammonium hydroxide is added in at least three portions; and/or viii) the temperature of step c) is maintained at about 25-35° C.

8. The LMWH of claim 4, wherein a) the weight average molecular weight of the LMWH is in the range of about 3-3.6 KDa; b) the LWMH exhibits a 1,6-anhydro residue content of about 2-13% or about 4-11% at the reducing terminus of its oligosaccharide chains; c) the LMWH exhibits a molar ratio of 1,6-anhydroglucosamine residues: 1,6 anhydromannosamine residues that is in the range of about 1:1 to about 3:1, about 1:1 to about 2.5:1, or about 1.05:1 to about 2.5:1; d) the LMWH exhibits an anti-FXa activity of about 80 IU/mg or more or in the range of about 80-120 IU/mg or about 95-120 IU/mg; e) the LMWH exhibits an anti-FIIa activity of about 5 IU/mg or more or in the range of about 5-20 IU/mg, or about 10-20 IU/mg; f) the LMWH exhibits a degree of coloration greater than or equal to 6 in the range of color reference solutions established in European Pharmacopoeia chapter 2.2.2 (method II) for at least 24 months or at least 36 months after storage at room temperature (about 20-22° C., or about 21° C.) at 60% relative humidity; g) the LMWH is included in a lyophilized composition; h) the LMWH is present as a sodium salt; h) the content of 1,6-anhydroglucosamine residues in the LMWH is less than about 1.1% mol; i) the content of 1,6-anhydromannosamine residues in the LMWH is less than about 1.2% mol; and/or j) the content of 1,6-anhydroglucosamine residues exceeds the content of 1,6-anhydromannosamine residues in the LMWH.

9. A low molecular weight heparin (LMWH) exhibiting a 1,6-anhydro residue content of about 1-15% at the reducing terminus of its oligosaccharide chains, a weight average molecular weight in the range of about 3-3.8 KDa, and a molar ratio of 1,6-anhydroglucosamine residues: 1,6 anhydromannosamine residues that is greater than or equal to about 1:1.

10. The LMWH of claim 9, wherein a) the weight average molecular weight of the LMWH is in the range of about 3-3.6 KDa; b) the LWMH exhibits a 1,6-anhydro residue content of about 2-13% or about 4-11% at the reducing terminus of its oligosaccharide chains; c) the LMWH exhibits a molar ratio of 1,6-anhydroglucosamine residues: 1,6 anhydromannosamine residues that is in the range of about 1:1 to about 3:1, about 1:1 to about 2.5:1, or about 1.05:1 to about 2.5:1; d) the LMWH exhibits an anti-FXa activity of about 80 IU/mg or more or in the range of about 80-120 IU/mg or about 95-120 IU/mg; e) the LMWH exhibits an anti-FIIa activity of about 5 IU/mg or more or in the range of about 5-20 IU/mg, or about 10-20 IU/mg; f) the LMWH exhibits a degree of coloration greater than or equal to 6 in the range of color reference solutions established in European Pharmacopoeia chapter 2.2.2 (method II) for at least 24 months or at least 36 months after storage at room temperature (about 20-22° C., or about 21° C.) at 60% relative humidity; g) the LMWH is included in a lyophilized composition; h) the LMWH is present as a sodium salt; h) the content of 1,6-anhydroglucosamine residues in the LMWH is less than about 1.1% mol; i) the content of 1,6-anhydromannosamine residues in the LMWH is less than about 1.2% mol; and/or j) the content of 1,6-anhydroglucosamine residues exceeds the content of 1,6-anhydromannosamine residues in the LMWH.

11. The LMWH of claim 10, wherein a) the content of 1,6-anhydroglucosamine residues in the LMWH is less than about 1% mol, or in the range of about 0.1-1% mol; i) the content of 1,6-anhydromannosamine residues in the LMWH is less than about 1.1% mol.

12. A low molecular weight heparin (LMWH) exhibiting a 1,6-anhydro residue content of about 1-15% at the reducing terminus of its oligosaccharide chains, a weight average molecular weight in the range of about 3-3.8 KDa, and a molar ratio of 1,6-anhydroglucosamine residues: 1,6 anhydromannosamine residues that is greater than or equal to about 1:1, wherein the LMWH has been prepared according to a process comprising the steps of a) providing benzalkonium heparin salt; b) depolymerizing said salt with three treatments with a quaternary ammonium hydroxide in methanol at 30±5° C. to form depolymerized heparin; and c) treating said depolymerized heparin one or more times with about 0.04-1 L of aqueous $H_2O_2$, which is about 30-35% wt/v in water, per Kg of depolymerized heparin to form said LMWH; wherein the heparin salt is a benzalkonium heparin salt.

13. The LMWH of claim 12, wherein a) the weight average molecular weight of the LMWH is in the range of about 3-3.6 KDa; b) the LWMH exhibits a 1,6-anhydro residue content of about 2-13% or about 4-11% at the reducing terminus of its oligosaccharide chains; c) the LMWH exhibits a molar ratio of 1,6-anhydroglucosamine residues: 1,6 anhydromannosamine residues that is or in the range of about 1:1 to about 3:1, about 1:1 to about 2.5:1, or about 1.05:1 to about 2.5:1; d) the LMWH exhibits an anti-FXa activity of about 80 IU/mg or more or in the range of about 80-120 IU/mg or about 95-120 IU/mg; e) the LMWH exhibits an anti-FIIa activity of about 5 IU/mg or more or in the range of about 5-20 IU/mg, or about 10-20 IU/mg; f) the LMWH exhibits a degree of coloration greater than or equal to 6 in the range of color reference solutions established in European Pharmacopoeia chapter 2.2.2 (method II) for at least 24 months or at least 36 months after storage at room temperature (about 20-22° C., or about 21° C.) at 60% relative humidity; g) the LMWH is included in a lyophilized composition; h) the LMWH is present as a sodium salt; h) the content of 1,6-anhydroglucosamine residues in the LMWH is less than about 1.1% mol; i) the content of 1,6-anhydromannosamine residues in the LMWH is less than about 1.2% mol; and/or j) the content of 1,6-anhydroglucosamine residues exceeds the content of 1,6-anhydromannosamine residues in the LMWH.

14. The LMWH of claim 12, wherein the process further comprises one or more of the following steps: a) precipitating said LMWH one or more times with a solution of sodium acetate in methanol; and/or b) converting a sodium heparin salt to said benzalkonium heparin salt.

15. The LMWH of claim 12, wherein said treating said depolymerized heparin salt one or more times with about 0.04-1 L of $H_2O_2$ step is conducted at a temperature of about 20-50° C. for a period of at least 3 h.

16. The LMWH of claim 12, wherein the process further comprises one or more of the following steps: a) after completion of the treating said depolymerized heparin salt one or more times with about 0.04-1 L of $H_2O_2$ step(s), adding a solution of sodium acetate in methanol, thereby precipitating crude LMWH sodium salt; b) lyophilizing a solution comprising the LMWH, thereby forming lyophilized LMWH; c) purifying the LMWH by way of a precipitation with a solution of sodium acetate in methanol; d) washing the quaternary ammonium heparin salt with aqueous solution prior to mixing it with benzyltrimethylammonium hydroxide; e) drying the quaternary ammonium heparin salt prior to mixing it with $CH_2Cl_2$ and/or benzyltrimethylammonium hydroxide; and/or f) isolating said LMWH as a LMWH sodium salt.

17. The LMWH of claim 16, wherein the process further comprises one or more of the following steps: i) dissolving the crude LMWH sodium salt in water and treating it with 0.09-0.07 L of $H_2O_2$ solution (about 33% w/v in water) per Kg of said depolymerized heparin salt at a temperature of at least 35-45° C. or 38-42° C. for a period of at least three hours, then neutralizing the solution with acid to a pH in the range of about 6-7.5, and adding methanol in the range of about 60-80% w/v relative to the water solution to form oxidized LMWH; or ii) dissolving the crude LMWH sodium salt in water and treating it with 0.06-0.04 L or 0.055-0.045 L of $H_2O_2$ solution (about 33% w/v in water).

18. The LMWH of claim 12, wherein a) the weight average molecular weight of the LMWH is in the range of about 3-3.6 KDa; b) the LWMH exhibits a 1,6-anhydro residue content of about 2-13% or about 4-11% at the reducing terminus of its oligosaccharide chains; c) the LMWH exhibits a molar ratio of 1,6-anhydroglucosamine residues: 1,6 anhydromannosamine residues that is in the range of about 1:1 to about 3:1, about 1:1 to about 2.5:1, or about 1.05:1 to about 2.5:1; d) the LMWH exhibits an anti-FXa activity of about 80 IU/mg or more or in the range of about 80-120 IU/mg or about 95-120 IU/mg; e) the LMWH exhibits an anti-FIIa activity of about 5 IU/mg or more or in the range of about 5-20 IU/mg, or about 10-20 IU/mg; f) the LMWH exhibits a degree of coloration greater than or equal to 6 in the range of color reference solutions established in European Pharmacopoeia chapter 2.2.2 (method II) for at least 24 months or at least 36 months after storage at room temperature (about 20-22° C., or about 21° C.) at 60% relative humidity; g) the LMWH is included in a lyophilized composition; h) the LMWH is present as a sodium salt; h) the content of 1,6-anhydroglucosamine residues in the LMWH is less than about 1.1% mol; i) the content of 1,6-anhydromannosamine residues in the LMWH is less than about 1.2% mol; and/or j) the content of 1,6-anhydroglucosamine residues exceeds the content of 1,6-anhydromannosamine residues in the LMWH.

19. The LMWH of claim 12, wherein said treating said depolymerized heparin one or more times about 0.04-1 L of aqueous $H_2O_2$ step is conducted at a temperature of about 20-50° C. for a period of at least 3 h.

20. The LMWH of claim 12, wherein the depolymerizing step comprises preparing an aqueous solution of heparin sodium, adding benzalkonium chloride to said solution to form benzalkonium heparinate, dissolving said benzalkonium heparinate in $CH_2Cl_2$, adding benzyltrimethylammonium hydroxide to the dissolved benzalkonium heparinate, thereby forming depolymerized heparin.

21. The LMWH of claim 20, wherein the process further comprises one or more of the following steps: a) after completion of the treating said depolymerized heparin one or more times about 0.04-1 L of aqueous $H_2O_2$ step(s), adding a solution of sodium acetate in methanol, thereby precipitating the LMWH; b) lyophilizing a solution comprising the LMWH, thereby forming lyophilized LMWH; c) after the treating said depolymerized heparin one or more times about 0.04-1 L of aqueous $H_2O_2$ step, adding a solution of sodium acetate in methanol, thereby providing said LMWH as LMWH sodium salt; d) purifying the LMWH by way of a precipitation with a solution of sodium acetate in methanol; e) washing the benzalkonium heparinate with aqueous solution prior to mixing it with benzyltrimethylammonium hydroxide; f) drying the benzalkonium heparinate prior to mixing it with $CH_2Cl_2$ and/or benzyltrimethylammonium hydroxide; and/or g) isolating said LMWH as a LMWH salt.

22. The LMWH of claim 12, wherein the quaternary ammonium hydroxide is selected from the group consisting of benzyltrimethylammonium hydroxide (Triton B) and benztriethylammonium hydroxide.

23. A low molecular weight heparin (LMWH) exhibiting a 1,6-anhydro residue content of about 1-15% at the reducing terminus of its oligosaccharide chains, a weight average molecular weight in the range of about 3-3.8 KDa, a molar ratio of 1,6-anhydroglucosamine residues: 1,6 anhydromannosamine residues that is greater than or equal to about 1:1, an anti-FXa activity of about 80 IU/mg or more, an anti-FIIa activity of about 5 IU/mg or more, and a degree of coloration greater than or equal to 6 in the range of color reference solutions established in European Pharmacopoeia chapter 2.2.2 (method II) for at least 24 months or at least 36 months after storage at room temperature (about 20-22° C., or about 21° C.) at 60% relative humidity.

* * * * *